US005792936A

United States Patent [19]

Dudits et al.

[11] Patent Number: 5,792,936
[45] Date of Patent: Aug. 11, 1998

[54] ZEA MAYS (L.) WITH CAPABILITY OF LONG TERM, HIGHLY EFFICIENT PLANT REGENERATION INCLUDING FERTILE TRANSGENIC MAIZE PLANTS HAVING A HETEROLOGOUS GENE, AND THEIR PREPARATION

[75] Inventors: Denes Dudits; Sandor Morocz; Janos Nemeth, all of Szeged, Hungary; Gunter Donn, Hofheim am Taunus, Germany

[73] Assignee: Hoechst Aktiengesellschaft, Frankfurt, Germany

[21] Appl. No.: 462,840

[22] Filed: Jun. 5, 1995

Related U.S. Application Data

[63] Continuation-in-part of Ser. No. 371,764, Jan. 12, 1995, abandoned, and a continuation-in-part of Ser. No. 184,365, Jan. 21, 1994, abandoned, which is a continuation of Ser. No. 43,594, Apr. 5, 1993, abandoned, which is a continuation of Ser. No. 719,316, Jun. 21, 1991, abandoned, said Ser. No. 371,764, is a continuation-in-part of Ser. No. 221,268, Mar. 31, 1994, abandoned, which is a continuation of Ser. No. 719,324, Jun. 21, 1991, abandoned.

[30] Foreign Application Priority Data

Jun. 23, 1990 [EP] European Pat. Off. ............ 90111945
Jun. 23, 1990 [EP] European Pat. Off. ............ 90111946

[51] Int. Cl.$^6$ ............................ A01H 5/00; A01H 4/00; C12N 5/04
[52] U.S. Cl. ................. 800/230; 800/200; 800/DIG. 56; 435/240.4; 435/240.49; 435/240.5
[58] Field of Search .................... 435/172.3, 172.1, 435/240.4, 240.45, 240.49, 240.5; 800/200, 205, 250, DIG. 56, 230

[56] References Cited

U.S. PATENT DOCUMENTS 4,975,374 12/1990 Goodman et al. ............. 435/172.3
5,220,114 6/1993 Martin .......................... 800/200

FOREIGN PATENT DOCUMENTS

B10619/88 7/1988 Australia .................. 435/172.3

OTHER PUBLICATIONS

Morocz et al. Improved system to obtain fertile regenerates via maize protoplast isolated from a highly embryopgenic suspension culture. TAG 80:721–726, 1990.
Shillito et al. Bio/technology vol. &:581–587, 1989.
Rhodes et al. "Genetically transformed maizeplants from protoplasts" Science 40:204–207, 1986.

*Primary Examiner*—Gary Benzion
*Attorney, Agent, or Firm*—Curtis, Morris & Safford, P.C.

[57] ABSTRACT

Protoplasts which regenerate reproducibly in a short time to normal, fertile plants can be regenerated from an auxin-autotrophic genotype of *Zea mays* (L.). Starting from immature embryos on hormone-free media, an auxin-autotrophic, embryogenic callus is formed on the shoot basis of the seedlings, which callus retains its embryogenic potential over a substantial period of time when subcultured on hormone-free medium. In addition to fully-developed embryos, adventitious embryos are also formed under suitable culture conditions (6–9% of sucrose in the medium). When the sucrose content is reduced to 2–3% and 2,4-dichlorophenoxyacetic acid is added, soft, granular calli are formed which consist of embryogenic cell aggregates (type II callus). After subculturing the type II callus in the form of a cell suspension culture, totipotent protoplasts can be isolated. From these protoplasts, the maize plants according to the invention are regenerated.

14 Claims, 8 Drawing Sheets

FIG. 3A

Phosphinothricin acetyltransferase gene sequence:

EcoRI
Promotor (7-536), Polylinker (537-576) and Terminator (577-771) (SEQ ID No:2)

```
GAATTCCCATGGAGTCAAAGATTCAAATAGAGGACCTAACAGATAGAACTCGCCGTAAAGACTGGCGAACAGTTCA    72
CTTAAGGGTACCTCAGTTTCTAAGTTTATCTCCTGGATTGTCTTGAGCGGCATTTCTGACCGCTTGTCAAGT
          12              24              36              48              60

TACAGAGTCTCTTACGACTCAATGACAAGAAGAAGAAATCTCGTCAACATGGTGGAGCACGACACGCTTGTCT   144
ATGTCTCAGAGAATGCTGAGTTACTGTTCTTCTTCTTTAGAAGCAGTTGTACCACCTCGTGCTGTGCGAACAGA
          84              96             108             120             132

ACTCCAAAAATATCAAAGATACAGTCTCAGAAGACCAAAGGCAATTGAGACTTTCAACAAAGGGTAATAT      216
TGAGGTTTTATAGTTTCTATGTCAGAGTCTTCTGGTTTCCCGTTAACTCTGAAAAGTTGTTTCCCATTATA
         156             168             180             192             204

CCGGAAACCCTCCTCGGATTCCATTGCCCAGCTATCTGTCACTTTATTGTGAAGATAGTGGAAAAGGAAGGTG    288
GGCCTTTGGGAGGAGCCTAAGGTAACGGGTCGATAGACAGTGAAATAACACTTCTATCACCTTTTCCTTCCAC
         228             240             252             264             276

GCTCCTACAAATGCCAATCATCATTGGCGATAAAGGAAAGGCCATGCGTTGAAGATGCCTCTGCCGACAGTGGTCCCA   360
CGAGGATGTTTACGGTTAGTAAACGCTATTTCCTTTCCGGTAGCAACTTCTACGGAGACGGCTGTCACCAGGGT
         300             312             324             336             348
```

FIG. 3B

```
AAGATGGACCCCCACCCCACGAGGAGCATCGTGGAAAAGAAGAGCGTTCCAACCACGTCTTCAAAGCAAGTGG
        372             384             396             408             420             432
TTCTACCTGGGGGTGGGTGCTCCTCGTAGCACCTTTTTCTTCTGCAAGGTTGGTGCAGAAGTTTCGTTCACC
ATTGATGTGATATCTCCACTGACGTAAGGGATGACGCACAATCCCACTATCCTCTTCGCAAGACCCTTCCTCTA
        444             456             468             480             492             504
TAACTACACTATAGAGGTGACTGCATTCCCTGCGTGTTAGGGTGATAGGAAGCGTTCTGGGAAGGAGAT
TATAAGGAAGTTCATTTCATTTGGAGAGGACAGGGTACCCGGGGATCCTCTAGAGTCGACCTGCAGGCATGC
        516             528             540             552             564             576
ATATTCCTTCAAGTAAAGTAAACCTCTCCTCCTAGGGCCCCTATGGGGCCTAGGGTAGCTGGACGTCCGTACG
CGCTGAAATCACCAGTCTCTCTCTACAAATCTATCTCTCTATAATAATGTGTGAGTAGTTCCCAGATAAG
        588             600             612             624             636             648
GCGACTTTAGTGGTCAGAGAGAGATCTTTAGATAAAGTATTATTACACACTCATCAAGGGTCTATTC
GGAATTAGGGTTCTTATAGGGTTTCGCTCATGTGTTGAGCATATAAGAAACCCTTAGTATGTATTTGTATTT
        660             672             684             696             708             720
CCTTAATCCCAAGAATATCCCAAAGCGAGTACACCACGAGTACACAACTCGTATATTCTTTGGGAATCATACATAAACATAAA
GTAAAATACTTCTATCAATAAAATTTCTAATTCCTAAAACCAAAATCCAGTGGGTACCGAGCTCGAATTCAA
        732             744             756             768             780             792
CATTTTATGAAGATAGTTATTTAAAGATTAAGGATTTTGGTTTTTAGGTCACCCATGGCTCGAGCTTAAGTT

```
          Met Ser Pro Glu Arg Arg Pro Val Glu Ile Arg Pro Ala Thr Ala
SalI
GTC GAC ATG TCT CCG GAG AGG AGA CCA GTT GAG ATT AGG CCA GCT ACA GCA
CAG CTG TAC AGA GGC CTC TCC TCT GGT CAA CTC TAA TCC GGT CGA TGT CGT
             12              24              38              48

Ala Asp Met Ala Ala Val Cys Asp Ile Val Asn His Tyr Ile Glu Thr Ser
GCT GAT ATG GCC GCG GTT TGT GAT ATC GTT AAC CAT TAC ATT GAG ACG TCT
CGA CTA TAC CGG CGC CAA ACA CTA TAG CAA TTG GTA ATG TAA CTC TGC AGA
         63              75              87              99

Thr Val Asn Phe Arg Thr Glu Pro Gln Thr Pro Gln Glu Trp Ile Asp Asp
ACA GTG AAC TTT AGG ACA GAG CCA CAA ACA CCA CAA GAG TGG ATT GAT GAT
TGT CAC TTG AAA TCC TGT CTC GGT GTT TGT GGT GTT CTC ACC TAA CTA CTA
         114             126             138             150

Leu Glu Arg Leu Gln Asp Arg Tyr Pro Trp Leu Val Ala Glu Val Glu Gly
CTA GAG AGG TTG CAA GAT AGA TAC CCT TGG TTG GCT GAG GTT GAG GGT
GAT CTC TCC AAC GTT CTA TCT ATG GGA ACC AAC CGA CTC CAA CTC CCA
         168             177             189             201
```

FIG. 4B

```
Val Val Ala Gly Ile Ala Tyr Ala Gly Pro Trp Lys Ala Arg Asn Ala Tyr
GTT GTG GCT GGT ATT GCT TAC GCT GGG CCC TGG AAG GCT AGG AAC GCT TAC
CAA CAC CGA CCA TAA CGA ATG CGA CCC GGG ACC TTC CGA TTG CGA ATG
216                 228                 240                 252

Asp Trp Thr Val Glu Ser Thr Val Tyr Val Ser His Arg His Gln Arg Leu
GAT TGG ACA GTT GAG AGT ACT GTT TAC GTG TCA CAT AGG CAT CAA AGG TTG
CTA ACC TGT CAA CTC TCA TGA CAA ATG CAC AGT GTA TCC GTA GTT TCC AAC
267                 279                 291                 303

Gly Leu Gly Ser Thr Leu Tyr Thr His Leu Leu Lys Ser Met Glu Ala Gln
GGC CTA GGA TCC ACA TTG TAC ACA CAT TTG CTT AAG TCT ATG GAG GCG CAA
CCG GAT CCT AGG TGT AAC ATG TGT GTA AAC GAA TTC AGA TAC CTC CGC GTT
318                 330                 342                 354

Gly Phe Lys Ser Val Val Ala Val Ile Gly Leu Pro Asn Asp Pro Ser Val
GGT TTT AAG TCT GTG GTT GCT GTT ATA GGC CTT CCA AAC GAT CCA TCT GTT
CCA AAA TTC AGA CAC CAA CGA CAA TAT CCG GAA GGT TTG CTA GGT AGA CAA
369                 381                 393                 405
```

FIG. 4C

```
Arg Leu His Glu Ala Leu Gly Tyr Thr Ala Arg Gly Thr Leu Arg Ala Ala
AGG TTG CAT GAG GCT TTG GGA TAC ACA GCC CGG GGT ACA TTG CGC GCA GCT
TCC AAC GTA CTC CGA AAC CCT ATG TGT CGG GCC CCA TGT AAC GCG CGT CGA
                420               432               444               456

Gly Tyr Lys His Gly Gly Trp His Asp Val Gly Phe Trp Gln Arg Asp Phe
GGA TAC AAG CAT GGT GGA TGG CAT GAT GTT GGT TTT TGG CAA AGG GAT TTT
CCT ATG TTC GTA CCA CCT ACC GTA CTA CAA CCA AAA ACC GTT TCC CTA AAA
            471               483               495               507

Glu Leu Pro Ala Pro Pro Arg Pro Val Arg Pro Val Thr Gln Ile Gly     SalI
GAG TTG CCA GCT CCT CCA AGG CCA GTT AGG CCA GTT ACC CAG ATC TGA GTC
CTC AAC GGT CGA GGA GGT TCC GGT CAA TCC GGT CAA TGG GTC TAG ACT CAG
        522               534               548               558
```

5,792,936

ZEA MAYS (L.) WITH CAPABILITY OF LONG TERM, HIGHLY EFFICIENT PLANT REGENERATION INCLUDING FERTILE TRANSGENIC MAIZE PLANTS HAVING A HETEROLOGOUS GENE, AND THEIR PREPARATION

RELATED APPLICATIONS

This application is a continuation-in-part of application Ser. No. 08/371,764, filed Jan. 12, 1995, now abandoned, which is a continuation-in-part of Ser. No. 08/221,268, filed Mar. 31, 1994, now abandoned, which is a continuation of Ser. No. 07/719,324, filed Jun. 21, 1991, now abandoned. This application is also a continuation-in-part of Ser. No. 08/184,365, filed Jan. 21, 1994, now abandoned, which is a continuation of Ser. No. 08/043,594, filed Apr. 5, 1993, now abandoned, which is a continuation of Ser. No. 07/719,316, filed Jun. 21, 1991. Foreign priority under 35 U.S.C.§ 119 to Ser. No. 07/719,316 is asserted to EPO Application NO. 01111946.1, filed Jun. 23, 1990 and EPO Application NO. 90111945.3, filed Jun. 23, 1990. Each of the above-mentioned U.S. and EPO applications are hereby incorporated by reference. Documents are cited in the following description and each of those documents are hereby incorporated herein by reference.

FIELD OF THE INVENTION

The invention relates to a genotype of Zea mays (L.) which is auxin-autotrophic and from which protoplasts, which reproducibly and stably regenerate into normal fertile plants, can be produced, as well as the regenerated plants and parts and progeny of those plants. Additionally, the invention relates to a novel maize genotype starting from immature embryos on hormone-free media from which an auxin-autotrophic embryogenic callus is formed on the shoot basis of the seedlings which develop.

BACKGROUND OF THE INVENTION

Despite the fact that several alternative approaches such as microinjection into the cells, macroinjection or bombardment with DNA coated particles of the intact or cultured tissues have been claimed as methods for genetic transformation of crop plants, according to the available experimental data protoplasts are ideal and the most widely used objects for parasexual genetic manipulation methods including DNA transformation and somatic hybridization. These genetic manipulations require a methodology for protoplast isolation and culture. For practical applications obtaining fertile regenerants from the manipulated protoplasts is a basic prerequisite. Among the monocotyledonous crop species maize is one of the most studied tissue cultures. Several publications have shown that the potential for plant regeneration from 20 various cultured organs including anthers and immature embryoids is highly genotype-dependent (Green and Phillips, Crop Sci. 15, 417 (1975), Morocz, Tag-Ber., Acad. Landwirtsch.-Wiss. DDR, Berlin (1983), Duncan et al., Planta 165, 322 (1985); each of which is incorporated herein by reference). Improvements of culture conditions can only partially overcome these limitations (Duncan et al., Planta 165, 322 (1985)).

Dicotyledon plants can essentially be transformed via Tiplasmid vector systems with the aid of *Agrobacterium tumefaciens*. However, this system cannot be applied readily to monocotyledon plants. Potrykus et al. (Mol. Gen. Genet. 199, 183 (1985); incorporated herein by reference) and L orz et al. (Mol. Gen. Genet, 199, 178 (1985); incorporated herein by reference) showed that plant protoplasts of monocotyledon plants can stably integrate foreign DNA into their genome. However, progress was first inhibited by the fact that the protoplasts could not be regenerated into fertile plants.

Over recent years there has been extensive research into the development of genotypes and processes to get the problem of plant regeneration under control. EP 29 24 435, incorporated herein by reference, relates to a process in which fertile plants can be obtained starting from a relatively non-mucilaginous, friable and granular maize callus. Shillito et al. (Bio/Technology 7, 581 (1989); incorporated herein by reference) have observed in this context that it is furthermore necessary for the regenerability into fertile plants to start from callus suspension cultures from which a dividing protoplast culture can be prepared which has the capability of regenerating plants. However, in this case, regenerable protoplasts could be isolated only after a long in vitro culture period of 7 to 8 months. Furthermore, the regenerated plants show abnormalities in morphology and fertility.

Prioli and Söndahl (Bio/Technology 7, 589 (1989); incorporated herein by reference) relates to the regeneration and production of fertile plants from maize protoplasts of the Cateto maize inbred line Cat 100-1. The authors assume that protoplast regeneration into fertile plants is a function of a number of various factors, for example genotype, physiological state of the donor cells and the culture conditions. However, in this case, regenerable protoplasts could be isolated only after a long in vitro culture period of 20 to 40 months. Furthermore, the regenerated plants also show abnormalities with regard to morphology and reproductivity.

Thus, it would be advantageous to develop a new Zea mays (L.) genotype which can produce tissue and cell suspension cultures with the reproducible capacity to regenerate stably plants which are normal and predominantly fully fertile.

OBJECTS AND SUMMARY OF THE INVENTION

It is thus a primary object of the invention to provide a new Zea mays (L.) genotype capable of producing tissue and cell suspension cultures with the reproducible capacity to regenerate stably plants which are normal and predominantly fully fertile.

It is a further object of this invention to provide a novel maize genotype starting from immature embryos on hormone-free media from which an auxin-autotrophic embryogenic callus can be formed on the shoot basis of the seedlings which develop.

It has now been surprisingly found that a new Zea mays (L.) genotype can produce tissue and cell suspension cultures with the reproducible capacity to regenerate stably plants which are normal and predominantly fully fertile.

The inventive novel maize genotype is distinguished from the previously described regenerable genotypes by the fact that, starting from immature embryos on hormone-free media, an auxin-autotrophic embryogenic callus was formed on the shoot basis of the seedlings which develop. This callus can be subcultured on hormone-free media over a prolonged period (>12 months) while maintaining its embryogenetic potential. Under these culture conditions, fully-developed embryos were formed which occasionally differentiate spontaneously into plants. Moreover, a large number of adventive embryos was formed, in particular when the sucrose content in the medium was increased (6–9%). The formation of soft, granular callus which was composed of embryogenic cell aggregates (type I callus), can be induced reproducibly by changing the medium (reduction of the sucrose content to 2–3% and addition of 1–3 mg/l 2,4-dichlorophenoxyacetic acid (2,4-D) or dicamba). This type II callus was sub-cultured in liquid media in the form of a cell suspension culture and was suitable for isolating totipotent protoplasts. The protoplasts can be used, inter alia, for genetic transformation and can be regenerated under the conditions described in the invention into fertile transgenic maize plants.

Thus, the invention relates to a transgenic, protoplast-derived maize cell line obtained from an auxin-autotrophic maize genotype, and transgenic plants and parts of plants, and their progeny, which have been regenerated from this maize cell line. Additionally, the invention relates to a method of producing the transgenic maize cell line which comprises producing protoplasts from cell suspensions of the maize genotype by means of enzymes, incubating the protoplasts with DNA and selecting and regenerating the transgenic maize cell line from the DNA-containing protoplasts.

The invention relates to a genotype of Zea mays (L.) which is auxin-autotrophic and from which protoplasts, which reproducibly and stably regenerate into normal fertile plants, can be produced, as well as the regenerated plants and parts and progeny of those plants; a protoplast produced from the genotype, as well as cells regenerated from this protoplast, said cells having the capability to regenerate a fertile plant; and a method for producing a callus culture of Zea mays (L.) from which protoplasts can be isolated, which protoplasts are capable of being regenerated into fertile plants, which method comprises the steps of a) obtaining callus which is auxin-autotrophic, relatively non-mucilaginous, granular and friable on a callus maintenance medium and b) growing the callus of step a) on a callus maintenance medium.

The invention further relates to a transgenic, protoplast-derived maize cell line which has been obtained from an auxin-autotrophic maize genotype, and transgenic plants and parts of plants, and their progeny, which have been regenerated from this maize cell line. Additionally, the invention relates to a method of producing the transgenic maize cell line which comprises producing protoplasts from cell suspensions of the maize genotype by means of enzymes, incubating the protoplasts with DNA and selecting and regenerating the transgenic maize cell line from the DNA-containing protoplasts.

The invention also relates to a genotype of Zea mays (L.) which is auxin-autotrophic and from which protoplasts, which reproducibly and stably regenerate into normal fertile plants, can be produced, as well as the regenerated plants and parts and progeny of those plants; a protoplast produced from the genotype, as well as cells regenerated from this protoplast, said cells having the capability to regenerate a fertile plant; and a method for producing a callus culture of Zea mays (L.) from which protoplasts can be isolated, which protoplasts are capable of being regenerated into fertile plants, which method comprises the steps of:

a) obtaining callus which is auxin-autotrophic, relatively non-mucilaginous, granular and friable on a callus maintenance medium and b) growing the callus of step a) on a callus maintenance medium.

The cell line DSM 6009 is a preferred representative of the genotype as characterized above and was deposited at the "Deutsche Sammlung von Mikroorganismen und Zellkulturen GmbH" on Jun. 1, 1990 under the conditions of the Budapest Treaty with the above-cited registration number.

The present invention, therefore, also relates to the cell line DSM 6009.

A method of producing the transgenic maize cell line which comprises
   producing protoplasts from cell suspensions of the maize genotype by means of enzymes,
   incubating the protoplasts with DNA and
   selecting and regenerating the transgenic maize cell line from the DNA-containing protoplasts.

BRIEF DESCRIPTION OF THE DRAWINGS

While the specification concludes with claims particularly pointing out and distinctly claiming that which is regarded as the present invention, the objects and advantages of this invention can be more readily ascertained from the following description of the invention when read in conjunction with the accompanying drawings in which:

FIGS. 3a–b shows the sequence for the phosphinothricin acetyltransferase gene under the control of the 35S promoter (SEQ ID NO.:1/SEQ ID NO.:2).

FIGS. 4a–c shows the phosphinothricin acetyltransferase gene cloned into the SalI cleavage site of pDH51, together with the sequence of the expression product (amino acid) (SEQ ID NO.:3/SEQ ID NO.:4/SEQ ID NO.:5).

DETAILED DESCRIPTION OF THE INVENTION

Figure 1A:
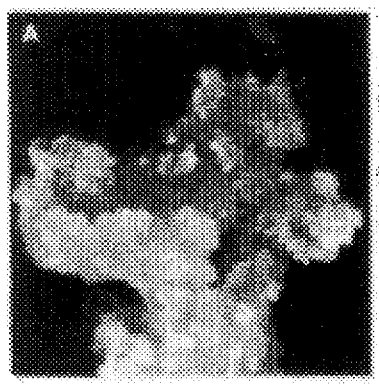
FIGS. 1A–1I and 1J: shows the various cell types and developmental stages involved in culturing DSM 6009, the DSM 6009 embryogenic maize culture and the regeneration of normal plants from it via the protoplast culture process.

It has now been surprisingly found that a new Zea mays (L.) genotype can produce tissue and cell suspension cultures with the reproducible capacity to regenerate stably plants which are normal and predominantly fully fertile.

Definitions

H 229: A regenerable haploid Zea mays (L.) tissue culture and genotype which was obtained via anther culture from MS Syn A/85 anther culture synthetic and which was produced by successive cross- and sib-pollinations with the inclusion of the following genotypes: A188, A629, GK3/H (inbreds), Black Mexican Sweet Corn (BMSC), Mangelsdorf's Tester (MT) (genetic stocks), white dent local variety (WDLV) and Golden Glow (GG) (local varieties). The H 229 culture is predominantly early-embryogenic, and readily forms suspension cultures, while the suspension culture protoplasts develop into plants under defined conditions. The H 229 plants obtained from the H 229 tissue culture are female-fertile, giving seeds upon pollination with viable pollen grains.

OK 281: A regenerable, predominantly early-embryogenic, somatic Zea mays (L.) tissue culture and genotype obtained via immature embryo culture from the MR Syn $So_2o_2/87$ which was produced by successive cross-, sib- and self-pollinations with the inclusion of the following genotypes: A188, GK3/H, W64A, Oh $43o_2o_2$ (inbreds), MT (genetic stock), white flint local variety (WFLV) (local variety) and H Temp $Ao_2o_2$ ($o_2o_2$ synthetic).

The OK 281 plants obtained from the OK 281 cultures produce seeds via self-, sib- or cross-pollination under appropriate conditions. The OK 281 genotype is homozygous for the recessive opaque gene ($o_2o_2$).

DSM 6009 (HE/89): A regenerable, highly embryogenic, predominantly early embryogenic somatic *Zea mays* (*L.*) culture and genotype obtained via immature embryo culture following cross-pollination between the two previously selected genotypes: H 229 and OK 281. The H 229 and OK 281 genotypes were maintained for 30 and 10 months, respectively, in culture before plants were regenerated for cross-pollinations. The DSM 6009 genotype is especially adapted to in vitro culture requirements as a consequence of its descent from ancestors which were selected for their tissue culture characteristics. Thus, DSM 6009 possesses a unique combination of the following traits:

1. Formation of hormone autotrophic embryogenic callus which grows well on standard plant tissue culture media.
2. Reproducible formation of callus-like early embryogenic (type II callus) cultures from mature somatic embryos on auxin-containing media.
3. Reliable long-term plant regeneration capability.
4. Reproducible conversion of callus-like early-embryogenic (type II callus) cultures into suspension cultures.
5. Abundant protoplast release one month after transfer of the callus into liquid culture.
6. High frequency of regeneration of fully fertile plants from callus, suspensions and protoplasts.

Early- and late-embryogenic cultures: A special type of maize (*Zea mays L.*) tissue cultures in which a rapid propagation rate of early stages of somatic embryos is observed. These embryoids do not mature into clearly visible embryoids which are characterized by their size, smooth, scutellum-like structures bearing leaf and root primordia. In contrast, the early-embryogenic cultures have the appearance of a homogeneous callus culture. This culture type is referred to as type II or friable embryogenic callus culture in the relevant literature. The early-embryogenic cultures develop into late-embryogenic cultures before plant regeneration. In the late-embryogenic cultures the embryoids are enlarged with well-developed scutellum-like bodies, green spots or leaf and shoot primordia, as well as with root primordia or small roots. In DSM 6009 cultures, both callus types are easily accessible and interchangeable depending on the culture conditions.

Somatic culture initiation and maintenance medium: The modified MS medium (Murashige, T. and Skoog, F. Physiol. Plant., 15 (1962) 473–497) as published by Green, C. E. and Phillips R. L. Crop Sci., 15 (1975) 417–421, hereby incorporated by reference, but with the following modifications and additions (final concentration in mg/l): Bacto tryptone 500 mg, L-asparagine 150 mg.

Anther culture initiation medium: N6 macro-elements, glycine and vitamins as in Chu et al., Scientia Sinica, 18 (1975) 659, MS micro-elements, EDTA and $FeSO_4 \cdot 7H_2O$ as in Murashige, T., and Skoog, F., Physiol. Plant, 15 (1962) 473, and the following components (per l): L-proline 100 mg, Bacto tryptone (BT) 600 mg, sucrose 120 g, benzyl-adenine 1 mg, naphthylacetic acid 1 mg, 2,4-dichlorophenoxyacetic acid (2,4-D) 2 mg, activated charcoal 5 g. The pH is adjusted to 5.8±0.05 with KOH before autoclaving and addition of activated charcoal. The medium is solidified with 5 g/l agarose.

Haploid culture maintenance medium: Macro-elements, micro-elements, EDTA, $FeSO_4 \cdot 7H_2O$, amino acids and vitamins as in the anther culture initiation medium. The altered components are (per l): 2,4-D 0.5 mg, sucrose 30 g, agar 8 g. The pH is adjusted to 5.8±0.05 before autoclaving.

Suspension culture (N6M)-medium: The same as the haploid culture maintenance medium without agar.

Protoplast culture medium (ppN6M) medium: A modified N6M-medium with the following additional ingredients or altered ingredients (final concentrations per l).

$MgSO_4 \cdot 7H_2O$: 370 mg; $CaCl_2 \cdot 2H_2O$: 300 mg; sucrose 1 g; glucose 50 g; fructose 30 g; maltose 2.5 g; galactose 2.5 g; galacturonic acid 500 mg; glucuronic acid 500 mg; L-asparagine 500 mg; L-glutamine 100 mg, L-serine 100 mg; 2,4-dichlorophenoxyacetic acid 0.4 mg; naphthylacetic acid 0.7 mg and zeatin (mixed isomers) 0.7 mg. The pH, without adjustment, is in the range of 4.5–5.0.

Protoplast isolation medium (cellulytic solution): 10 ml of the protoplast isolation solution are prepared from the following filter-sterilized (fs) or autoclaved (a) stock solutions:

| | |
|---|---|
| 0.3–0.5 ml | desalted cellulase/pectinase stock (fs) |
| 2.0 ml | washing solution (fs) |
| 4.2–4.4 ml | double-distilled $H_2O$ (a) |
| 0.5 ml | BSA stock solution (fs) |
| 0.1 ml | n-PG solution (fs) |
| 0.1 ml | 1 M $CaCl_2$ solution (a) |
| 0.1 ml | 1 M $MgSO_4$ solution (a) |
| 2.5 ml | osmotic solution (fs) |

Desalted cellulase/pectinase stock solution: 10 g Cellulase Onozuka RS and 1 g Pectolyase Y23 are dissolved in double-distilled $H_2O$ at 4° C. Insoluble debris is removed by centrifugation (6000 rpm for 10 min). The supernatant is desalted by running through a Sephadex G25 column (column volume 200–250 ml). The salt-free enzyme-containing fractions are pooled and adjusted to a final volume of 50 ml. They are filter-sterilized through 0.22 μm membrane filters and then deep frozen in 0.5 ml aliquots.

Washing solution (WS): N6M medium without Fe, EDTA, 2,4-D and $(NH_4)_2SO_4$. It contains the following sugars: sucrose 10 g/l, glucose 55 g/l and fructose 55 g/l.

BSA - Stock solution: From lyophilized bovine serum albumin, fraction V (Merck®), a stock solution is prepared, containing 40 mg BSA in 1 ml double-distilled $H_2O$. Aliquots are kept deep frozen prior to use.

nPG - solution: 50 mg n-propyl gallate are dissolved in 2 ml ethanol. 8 ml double-distilled $H_2O$ are added and the solution is filter-sterilized. 1% freshly prepared nPG solution is added to the washing solution (WS-nPG) and 0.6M sucrose solution (0.6 Su+nPG).

Osmotic solution: 100 ml contain $KNO_3$ 4.04 g; $KH_2PO_4$ 2.72 g; $K_2HPO_4$ 0.94 g; fructose 7.2 g; glucose 8.0 g; L-proline 0.68 g. The solution is filter-sterilized.

The genotypes as characterized above and the techniques of culture initiation and maintenance, the suspension culture establishment, the protoplast isolation and culture techniques were developed in the following steps:

Step (a): Evaluation of a Wide Range of Commonly Used Genotypes for Tissue Culture Potential Maize inbreds, stocks and land races were tested for their ability to form callus cultures from anthers and somatic organs such as immature embryos, apical and lateral meristems. For anther culture, anthers with mononucleate microspores were placed onto anther culture initiation medium and were incubated in the dark preferably at 21° to 28° C. for 40 to 90 days.

For somatic cultures the inocula (e.g. 1 to 3 mm size immature embryos, 0.5 to 0.7 cm size meristems), either intact or sliced were placed on somatic culture initiation and maintenance medium in the light at 21° to 28° C. for 30 to 60 days. The resulting cultures were tested for their ability to regenerate on plant regeneration medium. The genotypes responding with regenerable tissue cultures were used for cross-hybridization, and the hybrid embryos were tested in the same way with additional scoring for their regenerability followed by at least one year of maintenance in tissue culture. The material derived from anther culture was maintained on haploid-maintenance medium. The hybrids of regenerable inbreds, stocks or land races usually produced embryogenic cultures with increased frequency. They did not lose the ability to regenerate after the first few passages and were more easily regenerated to plants from their tissue cultures than their parents.

Step (b): Production of Starting Synthetics from the Genotypes Selected in Step (a)

Several genotypes from cultured anthers and somatic inocula that proved to be regenerable in step (a) were crossed through successive generations to obtain synthetics for anther and somatic tissue cultures, each with the involvement of 6 to 8 genotypes.

Step (c): Selection for Improved Recombinants with Superior Tissue Culture Properties Anthers and immature embryos or meristems from synthetics as described under step (b) were used as inocula to obtain improved regenerable embryogenic cultures. Out of several hundreds of regenerable cultures a special type of culture was obtained which can be maintained as an early embryogenic, abundantly proliferating callus. After one year of maintenance, genotypes like H 229 and OK 281, the parent genotypes of DSM 6009, were obtained by selecting and keeping only those cultures which produce normally developing regenerants from calli grown both in surface and in suspension culture. The isolated protoplasts of these selected fertile, regenerable, early embryogenic cultures again showed variation in their viability and culturability. Genotypes with positive responses in protoplast experiments were preferably kept. After the selection process, regenerants from the first cycle genotypes were cross-hybridized to obtain second cycle genotypes, such as DSM 6009 (HE 89), that were equally well-suited for the initiation of regenerable haploid or somatic cell and tissue cultures, and produced totipotent protoplasts from appropriate cultures.

Step (d): Optimization of the Conditions for Regulation of the Developmental Stages of the Genotype in the Selected Cultures Frequent and regular passages (2 to 3 times at 1 to 2 week intervals) of the H 229, OK 281 and DSM 6009 tissue cultures on maintenance media suppressed further differentiation of the early embryoids and caused redifferentiations of the later developmental stages to the early stages. Once the homogeneous early-embryogenic culture was obtained, it was easily maintained on different culture media at less frequent passage intervals (e.g. 1 month). With infrequent passages or preferably on transfer to plant regeneration medium, later-embryogenic cultures developed from the early embryogenic cultures. The late-embryogenic cultures consisted of a synchronously germinating embryoids which, after a second transfer onto plant regeneration medium, yielded a large number of regenerated plants. The early-embryogenic cultures of these genotypes were characterized by their high flexibility in respect of culture media. Commonly used culture media, such as MS (Murashige/Skoog, Physiol. Plant 15, 473 (1962)), B5, SH or N6 (Chu C. C. et al., Sci. Sin. 16, 659 (1975)) can all be used to initiate or maintain H 229, OK 281 and DSM 6009 tissue cultures. The N6M medium was preferred because it was possible to maintain these cultures without the loss of capability for fertile plant regeneration for several years on this medium (e.g. for 4 years in the case of H 229). The close interaction between the high-level expression of the embryogenic traits in these genotypes and the optimal composition of the N6M medium for the manifestation of the regenerable, embryogenic culture formation was demonstrated by the applicability of N6M medium without hormones not only for plant regeneration but also for initiation and maintenance of embryogenic cultures from these genotypes. As a consequence, an important characteristic of these genotypes was their auxin-autotrophic growth capability.

Step (e): Improvement of Maintenance of the Suspension Cultures Which Allow the Regeneration of Fertile Plants After Prolonged Periods of Culture Due to the fact that fast growing cell populations have the tendency to accumulate cellular mutants, there was a need to improve the liquid culture medium in order to extend the time during which a suspension culture can be regenerated into phenotypically normal and fully fertile plants. Unexpectedly, it was found that this can be achieved by replacement of N6-micronutrients by MS-micronutrients and by decreasing, compared to surface cultures, the 2,4-dichlorophenoxyacetic acid (2,4-D) content and increasing sucrose (the latter to about 3% in the medium. This so-called N6M medium was also suitable for the friable early embryogenic callus culture of DSM 6009. After about 2 passages in this medium, the suspension could be used to isolate in good yield regenerable protoplasts from this genotype.

Step (f): Protoplast Isolation and Culture

Protoplasts from the genotypes described were produced by incubation with lysing enzymes, such as cellulases and pectinases. The enzymes can also be used as mixtures, the concentration of a single enzyme being 0.05 to 4% (weight per volume). The optimal composition of the aqueous incubation solution as well as enzyme concentration was established for each type of tissue in simple tests. For osmotic stabilization of protoplasts, the incubation solution should contain osmotic substances such as mannitol, sorbitol, glucose, sucrose, fructose, $KNO_3$ or other typical salts of plant nutrient media. The osmolarity of the enzyme solution was preferably in the range from 500 to 750 mOsm, in particular in the range from 600 to 700 mOsm. The pH can vary in the range from 4.5 to 6.0. Preferably the pH was in the range from 5.5 to 6.0 and was stabilized by addition of 1 to 75 mM phosphate and 1 to 10 mM morpholinoethanesulfonic acid (MES).

Depending on the enzyme concentration, protoplasts were produced after 3 to 20 hours. During incubation careful suspension by shaking was preferred, in particular on an orbital shaker at 10 to 50 rpm.

After incubation the protoplasts can be transferred to a growth medium containing salts, vitamins, amino acids, a synthetic auxin, like 2,4-D or dicamba, as well as sugars, preferably a mixture of fructose, glucose and sucrose.

Most preferably the protoplasts were cultured in thin layers (e.g. 0.1–1 mm) of ppN6M protoplast culture medium in sterile glass or plastic culture vessels, sealed properly to prevent evaporation from the protoplast cultures, in dim light at temperatures between 21° to 26° C. The density of protoplasts necessary for cell and colony formation was between $5-7\times10^5$ and $3-5\times10^6$ protoplasts per ml of protoplast culture medium. After a culture period of 20 to 40 days, colonies visible to the unaided eye develop in the protoplast culture medium. The period necessary for the formation of visible colonies may be shortened by the stepwise addition of small amounts of suspension or protoplast culture medium (e.g. 0.2 to 0.5 ml at 3–4 day intervals) three weeks after the start of the protoplast culture. The visible colonies were placed on maintenance or regeneration medium or alternatively may be used to start a new suspension culture.

Step (g): Plant Regeneration and Growth of the Regenerated Plants to Maturity from Protoplast-Derived Cultures The protoplast-derived colonies were placed on plant regeneration medium, where they developed into mature somatic embryos which eventually germinate into plantlets. On hormone-free media, the relatively homogeneous early embryogenic cultures formed on their surface well developed embryogenic tissue clusters. When the mature and germinating, embryoids were placed on fresh hormone-free plant regeneration medium a large number of healthy plants differentiate. When the plantlets had a size of 5 to 7 cm and several roots at the first nodes, they were removed from the culture vessel and separated from each other and from the adhering agar pieces. Their root system was freed from weak non-nodal roots and culture medium using tap water. The plantlet was then transplanted into soil. An appropriate soil was an equal part mixture of peat, sand and perlite or any commercially available horticulture soil. The plants were grown under nylon bags or in a humid atmosphere for ten days, illuminated constantly for two days and periodically afterwards with an intensity to provide normal green coloration and vigorous growth of the plants. The plants were watered and nourished with fertilizers regularly to ensure their normal growth and development. Only the carefully cultivated plants that retain the green color of their first leaves were used to produce seeds via self- or cross-pollination. Most of the plants that were transplanted into soil before ageing starts in the culture vessels and which were cultivated properly produced well-developed plants devoid of abnormalities in the reproductive organs.

Step (h): Strain Identification and Genotype Protection with the Aid of RFLP (Restriction Fragment Length Polymorphism)

Figure 2:
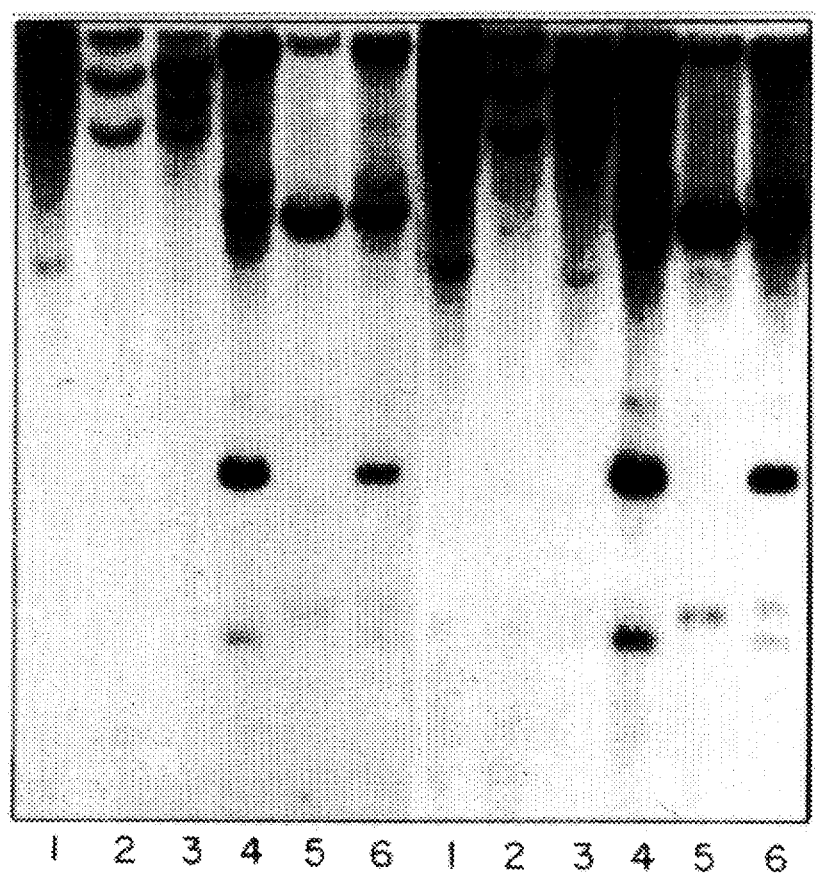
FIGS. 2a–b shows all of the analyzed genotypes where restriction fragment polymorphism is visible after hybridizing with a 32P-labeled cDNA insert for a putative auxin receptor gene.

In addition to the typical morphological and physiological traits as they become visible in tissue culture initiation and maintenance, plant regeneration and plant stability characteristics of the selected genotypes and the distribution of hybridizing restriction fragments after the use of defined molecular probes allowed the identification of the described genotypes. DNA was isolated from the parental lines (H 229 and OK 281) and the resulting highly embryogenic hybrid DSM 6009. For example, the hybridization patterns after digestion of this plant DNA with HindIII and BamHI restriction enzymes by using a cDNA clone for a putative auxin receptor gene cloned from maize (U. Tillman et al. The EMBO J. 1988, 2463–2467) are shown in FIGS. 2a–b. As can be seen in FIGS. 2a–b, all of the analyzed genotypes exhibit a unique and characteristic pattern of hybridizing bands.

FIGS. 2a–b show restriction fragment polymorphism visible after hybridizing with a 32P-labeled cDNA insert for a putative auxin receptor gene (U. Tillmann et al. The EMBO J. 1988, 2463–2467; incorporated herein by reference) where:

| | |
|---|---|
| 1 | OK |
| 2 | H 229 HindIII |
| 3 | DSM 6009 |
| 4 | OK |
| 5 | H 229 BamHI |
| 6 | DSM 6009 |

The exposure time of FIG. 2b was approximately 3 times longer than of FIG. 2a.

The protoplasts were prepared from DSM 6009 with the aid of lysing enzymes, for example cellulases and pectinases, it also being possible for the enzymes to be used in the form of mixtures. The concentration of the enzyme can vary within wide limits from 0.05–4% (weight per volume of enzyme solution). The optimum composition of the aqueous osmotic solution as well as the enzyme concentration must be determined for each type of tissue by simple tests.

To stabilize the protoplasts, the aqueous solution must contain osmotically active substances such as mannitol, sorbitol, glucose, sucrose, fructose, $KNO_3$, or other salts which are typical of plant media. The osmolarity of the enzyme solution was advantageously between 500 and 750 mOsm, preferably between 600 and 700 mOsm. The pH can vary between pH 4.5 and 6.0. The pH of the enzyme solution was preferably adjusted to 5.5 to 6 and stabilized using 1 to 5 mM phosphate and 1 to 10 morpholino-ethanesulfonic acid (MES).

Depending on the concentration of the lysing enzymes, the protoplasts emerged in the course of 3–20 hours. Careful shaking during enzyme incubation was advantageous. Shaking on an orbital shaker at 10–50 rpm has proved advantageous.

Any DNA can be introduced into the cell. It was advantageous to work with selectable marker genes, for example the gene for phosphinothricin acetyltransferase, acetyl-CoA carboxylase, glutathione S-transferase, hygromycin phosphotransferase, acetolactate synthetase, 5-enolpyruvyl-shikimate-phosphate synthetase (PSP synthetase), glutamine synthetase or transaminase. Of course, it is also possible to introduce genes whose expression cannot be selected by the growth of the plant. Genes of this type can, for example, encode the δ-endotoxin of *Bacillus thuringiensis* or virus resistance, for example genes for virus "coat" proteins. Furthermore, the chitinase gene, or genes, which improve the photosynthetic performance of the plant, can be employed, for example the gene for phosphoenolpyruvate carboxylase or bacterial asparagine synthetase (Nakamura, M. M. et al. Nucleic Acids Research 9, 4669 (1981); incorporated herein by reference). It was preferred to use the gene for phosphinothricin acetyl-transferase from *Streptomyces viridochromogenes* (Wohlleben, W. et al., Gene 80, 25–57 (1988); incorporated herein by reference) which can be modified appropriately for expression in plants. By incorporating this gene, the maize plants and their progeny become resistant to phosphinothricin (glufosinate) and phosphinothricinalanylalanine (bialaphos).

After synthesis, or isolation, the gene can be multiplied by conventional methods, for example by transformation of *E. coli* or by "polymerase chain reaction". The isolated, functional gene can then be introduced into the protoplasts directly or on any desired cloning vector, advantageously pBR 322, pUC 18 or pDH 51 (Pietrzak, M. et al. Nucl. Acid Res., 14, 5858 (1986); incorporated herein by reference), with or without a promoter which is effective in plants. The promoter which was preferably used was the 35 S promoter. The DNA can also be employed in the form of a complex with histones, as is described, for example, in German Patent Application 40 05 152.8, hereby incorporated by reference.

For protoplast inhibition, the DNA was suspended in aqueous solution, which can also contain buffer salts, and the suspension was added to the protoplasts which were in a transformation buffer which acts as an osmotic.

The transformation buffer comprised an aqueous solution of salts, preferably of divalent cations such as $MgCl_2$ or $CaCl_2$, or of their mixtures, or, alternatively, of sugars such as sucrose, glucose or fructose, or sugar alcohols, for example mannitol or sorbitol. In the transformation buffer, the salts were present in an amount of from 30–300 mval, and the sugars, or the sugar alcohols, in a concentration of from 50 to 500 mmol.

After the DNA solution was added to the protoplasts, polyethylene glycol, preferably PEG 1500 to 8000, was added to the mixture so that the final concentration was approximately 10 to 25% by weight, preferably 6 to 10% by weight per liter of mixture. Incubation was then carried out at a pH of from 6.0 to 8.0, preferably 6.5 to 7, and a temperature from 15° to 40° C., preferably 20° to 25° C. over a period of 5 minutes up to one hour, preferably 20 to 30 minutes. When the incubation ended, the cells were advantageously transferred to a growth medium which contained inorganic salts, for example ammonium salts, potassium salts, calcium salts and magnesium salts, and also nitrate, phosphate, sulfate, dihydrogen phosphate, citrate, vitamins, amino acids, a synthetic auxin, for example 2,4-D or dicamba, and also sugars, preferably a mixture of fructose, glucose and sucrose, after previously removing the PEG by one or more washing operations.

After 10 to 25 days, the surviving and dividing cells were cultured on a selection medium. For osmotic stabilization of the protoplast calli, the medium should advantageously contain 6 to 10% sugar, in particular sucrose. The older the protoplast culture is, the lower the sugar content may be. For example, a medium containing approximately 9% sugar was suitable for a 15–20 day old protoplast culture. The selection medium had essentially the same composition as the above-described growth medium, and contained a selection agent, for example phosphinothricin. The selection was carried out as described, for example, in EP 0 290 987, hereby incorporated by reference.

On the medium described, the transformed protoplasts developed into cell clusters which expressed the gene and which then grew into macroscopically visible calli.

About 14 to 28 days after the selection has been started, the calli were transferred to fresh, preferably hormone-free selection medium so as to make possible embryo maturation. During the subsequent culture, the transgenic embryos formed can differentiate leaves and roots, with or even without selection agent in the medium.

As soon as the in vitro plants have reached a size of 4 to 8 cm, they were planted in soil and grown in a controlled-environment cabinet or in the greenhouse into flowering plants. The fertile, transgenic maize plants can be propagated either by self-pollination or by cross-pollination, i.e. by crossing with elite inbred lines.

The invention also relates to a method of protecting monocotyledon plants, by selective destruction of weeds with phosphinothricin or phosphino-thricinalanylalanine, by planting areas under cultivation with plants which can be obtained from the method according to the invention and which contain the phosphinothricin acetyltransferase gene, and with their progeny.

The invention is described in greater detail in the following, non-limiting examples:

EXAMPLES

Example 1

Production of the Opaque Somatic Culture Synthetic MR Syn $So_2o_2/87$ and the Predominantly Early-Embryogenic Culture OK 281

Plants from different maize genotypes were grown in the field. Three to four plants were self-pollinated and the fertilized ears were harvested 12–14 days after pollination. After removal of husks and silks, the ears were surface sterilized in 0.15% sodium hypochlorite solution containing 0.5% household detergent for 10 minutes followed by rinsing 3 times with sterile deionized water. Ten embryos per ear were then aseptically dissected and placed with their flat plumule and radicle side down in contact with the surface of 50 ml solidified (0.8% agar) somatic culture initiation and maintenance medium in 10×2 cm petri dishes. The embryo cultures were incubated for 30–60 days under illumination at $25°\pm2°$ C. After evaluation, the embryogenic cultures were transferred to fresh medium at monthly intervals and tested for plant regeneration capacity on plant regeneration medium. From the tested genotypes, the inbreds A188, GK3/H and W64A, the genetic stock Mangelsdorf's Tester (MT) and a white flint local variety (WFLV) were found to form regenerable cultures under the described conditions. These genotypes, however, formed predominantly late embryogenic cultures, often referred to as type I culture in the maize tissue culture literature. Their regenerative potential gradually decreased upon successive transfers to fresh medium and after 6 months maintenance only occasional small regenerable sectors were present. When hybrids of two regenerable genotypes were produced and their embryo cultures were tested in the same way, an improvement in the propagation rate and regenerability was observed. The culture from the A188×W64A hybrid, for example, was maintained for 3 years without the loss of regenerative potential. To facilitate further combination of the possible advantageous genes from the original genotypes, a multiple-generation crossing program was started. Two opaque ($o_2o_2$) sources which were either non-regenerable under those conditions (Oh $43o_2o_2$) or not tested for their ability to regenerate from tissue cultures (H Temp $Ao_2o_2$) were included. To combine the opaque gene with the genes responsible for the regenerable trait, first the opaque source genotypes had to be crossed with the regenerable genotypes. Therefore, these genotypes were planted, cultivated and their ears were isolated before silk emergence. The isolated ears of the regenerable genotypes were cross-pollinated with pollen from genotypes carrying the opaque gene. Thus, the single cross hybrids (SC1–SC10) were obtained by crossing A188, GK3/H, W64A, MT, and WFLV with Oh $43o_2o_2$ and H Temp $Ao_2o_2$.

The kernels of these ten different single crosses were harvested, planted, grown and isolated as before for the second series of cross-pollinations to obtain the double cross (DC1–DC5) hybrid kernels from SC1×SC7, SC2×SC8, SC3×SC9, SC4×SC10 and SC5×SC6 crosses, respectively. From the first and second pollination series, only one harvested ear was taken from each cross-pollination for further generation. From the harvested DC kernels, homozygous $o_2o_2$ kernels were selected on the basis of their phenotype and were planted. At the flowering time in a third pollination series, each DC hybrid (DC1 to DC5) was crossed with all the others to provide 4 harvested ears from each of the 20 cross-combinations. From the resulting 80 ears, ten kernels per ear were bulked, planted and randomly sib-pollinated to give a possibility for recombination of the desired genes. Of the hundred best ears were taken from the sibbed, harvested plant material, ten kernels from each ear were bulked and regarded as a starting somatic culture synthetic (MR Syn $So_2o_2$/87). The obtained synthetic was planted and the flowering plants were self-pollinated. From each of 100 self-pollinated ears, ten immature embryos were plated in the described manner. About 30 percent of the cultured embryos (286 out of 950) produced regenerable cultures with the majority of them being the late-embryogenic type. From the spontaneous early-embryogenic cultures obtained, often referred to as type II or friable embryogenic culture in the relevant literature, the OK 281 culture was selected on the basis of its vigorous growth, lack of necrosis, easy regenerability into plants and fertility of regenerated plants.

Example 2

Production of the Anther Culture Synthetic MR
Syn A/85 and the Early-Embryogenic Haploid
Culture H 229

Different maize genotypes were planted and cultivated to the appropriate physiological stage to collect tassels with the uppermost leaves uncovered. The outer leaves were unfolded and discarded. The remaining tassels still in the covering whorl were put into plastic bags and cold treated at a temperature of 4° to 8° C. in the refrigerator for 10–30 days. After this treatment, the covering leaves were removed and the tassel sectors with anthers carrying late mononucleate microspores were selected using microscopic examination of anthers squashed in 2% aqueous orcein solution. The florets carrying the desired microspores were surface sterilized in 0.1% sodium hypochlorite solution containing 0.5% household detergent for 10 minutes followed by rinsing the florets in deionized sterile water 3 times for 10 minutes. From the surface sterilized florets, about 100 anthers were dissected and placed on 50 ml anther culture initiation medium in 10×2 cm glass Petri dishes. The plated anthers were incubated in the dark for 40–90 days at 25° C. Two local varieties, the Golden Glow (GG) and a white dent local variety (WDLV), produced at low percentage (below 1%) haploid calli from the cultured anthers. None of them regenerated plants on the regeneration medium. The two local varieties (GG and WDLV) were crossed and the hybrid kernels were planted and anthers of the resulting F1 plants were tested in the same way. From the obtained haploid embryoids, one culture could be used for multiple plant regeneration during a period of one year before it lost its regenerative potential. To combine the embryoid formation potential, the plant regeneration capacity and plant characters necessary for the survival and growth of the regenerants transplanted into the soil, ten plants from the hybrid of the two local varieties were cross-pollinated with a plant population obtained by the cross-hybridization of two independent hybrids [GK3/H×MT and (A188×A619)×BMSC] each of which was found to respond in anther culture. Ten kernels from the harvested ears were bulked, planted in the field and the plants selected for absence of undesirable agronomic traits (such as tillering, smut, lodging) were sibbed. After harvesting, the 30 best ears were kept and used for bulking an equal number of kernels per ear. These bulks represented the anther culture synthetic MR Syn A/85. One bulk of the synthetic was planted, and tassels were collected and processed in the described manner. From the cultured anthers a response of 0 to about 20% of embryoid formation was observed per Petri dish. Out of more than 300 haploid embryoids derived from different tassels of the MS Syn A/85, about 20% developed into regenerable embryogenic cultures after transfer from the initiation medium to haploid maintenance medium. From the regenerable cultures, the H 229 culture was selected on the basis of its predominantly early-embryogenic callus phenotype, its fast propagation rate, its plant regeneration capacity after long-term surface and suspension culture (more than two years before using for further crossing cycle) and its ability to divide and to form colonies and to regenerate plants from protoplasts.

Example 3

Production of the Highly Embryogenic Culture
DSM 6009

Two previously selected genotypes developing predominantly early-embryogenic culture from embryos or anthers were cross-pollinated in order to combine the desirable characteristics of both. Female flowers of the regenerated H 229 plants, 30 months after initiation, were pollinated with the pollen from OK 281 plants regenerated 10 months after initiation. The obtained immature hybrid embryos were incubated on somatic culture initiation and maintenance medium as well as on plant regeneration medium. One of the embryos forming early-embryogenic culture on the plant regeneration medium, DSM 6009 (HE 89) was selected, maintained and used to initiate suspension cultures. Only two months after inoculation of the donor hybrid embryo (HL29×OK281), the first successful protoplast culture was started, which led to the formation of fertile protoplast-derived plants. DSM 6009 has all the desirable features of its parents and was superior to them in many tissue culture traits listed earlier.

Example 4

Evaluation of the Suspension Culture Medium
N6M for the Retention of Regenerability in the
Selected Maize Tissue Cultures Since the development of the suspension culture medium N6M, three independently selected regenerable genotypes (including early- and late-embryogenic, somatic and haploid cultures) have been tested for more than two years in suspension culture for their regenerative and fertility properties. The 4C1 somatic mainly late-embryogenic culture, the C2-A somatic, late embryogenic culture, and the H 229 haploid mainly early-embryogenic culture were maintained in N6M suspension culture medium. Although suspension cultures showed a faster propagation rate, the plant regeneration capacity of these selected genotypes was better when the embryoids were plated from suspension cultures than from infrequently passaged (about 2-month intervals) agar surface cultures. In all three cases, after two years of maintenance in N6M suspension culture fertile plants could be obtained. Similar observations were made with other cultures after one year of maintenance in this suspension culture. Therefore, N6M suspension culture medium was preferred for maintenance of the cultures before protoplast isolation.

Establishment and Maintenance of HE/89
Suspension Culture

The less than 1 mm embryos (H 229×OK 281) obtained from a greenhouse-grown plant 12 days after pollination were incubated on N6M without 2,4-D for 3 weeks followed by two subcultures on N6M and MSG medium at 10–14 day intervals before the suspension culture was started in N6M medium. For regular maintenance, four grams of cells were used to start a new culture cycle of 5–7 days in 50 ml N6M medium in 100 ml Erlenmeyer flasks. All the cultures were grown under continuous or periodic illumination by fluorescent tubes at 22°–25° C.

Protoplast Isolation and Culture

Two grams of fresh-weight cell material from suspension cultures 2 days after the last transfer was crushed with forceps in 1 ml washing solution (WS), to which 1% of nPG stock solution was added. This treatment reduced the size of the 2 to 3 mm colonies. The crushed cell suspension was washed twice with nPG-WS. The washed cells were incubated in 10 ml protoplast isolation medium for 4 hours in the dark with or without gentle shaking. After enzyme treatment, the solution was passed through a 210 micron and 60 micron screen followed by centrifugation at 1000 rpm. The pellet was resuspended in 10 ml of 0.6M sucrose+nPG and 1 ml of WS+nPG was overlaid for the second centrifugation. The floated protoplasts were collected and sedimented again in 15 ml WS+nPG in the third centrifugation. The number of protoplasts was counted using a Buerker or Thoma chamber before the third centrifugation. The protoplasts were cultured in 2 ml of liquid medium or were embedded in 0.5–0.7% low gel point agarose (Sigma) by mixing the protoplasts gently with 2 ml of double strength ppN6M (1:1 ppN6M/89:HE/89) and 1.2% melted agarose solution after a previous temperature adjustment to 45° C. for both solutions. The protoplasts were cultured under dim light at 25° C. For feeding the protoplasts in the liquid medium, the 0.5 ml N6M medium was added after 3 weeks, followed by the addition of a further 1 ml 2–3 days later. Then after 3–4 days, the whole culture was put into 10 ml fresh N6M medium and was shaken. The agarose embedded cultures were placed either on solidified N6M with or without 2,4-D or into 10–50 ml liquid N6M medium after 2–4 weeks, in most cases after 3 weeks.

Plant Regeneration and Growth

From the regenerated calli on agar medium 0.2–1 g of embryogenic callus was placed on 100 ml of N6M lacking 2,4-D in glass jars with a lid containing an aerating sponge plug or in plastic containers. This step was repeated until well-developed plants were obtained from the embryoids and the plantlets. The bigger plants (above 7 cm) were removed for transplantation into pots of different sizes containing various kinds of horticultural soils rich in humus. The plants with emerged silks and pollen-shedding tassels were self- or sib-pollinated.

Figure 1B:
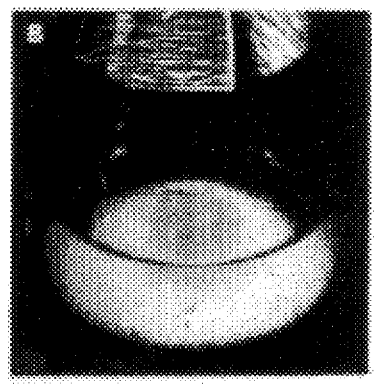
Figure 1C:
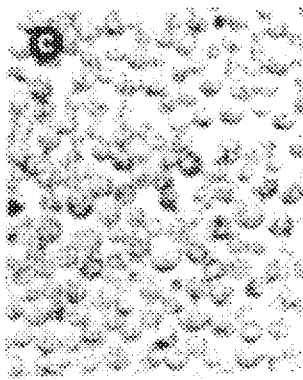
Figure 1D:
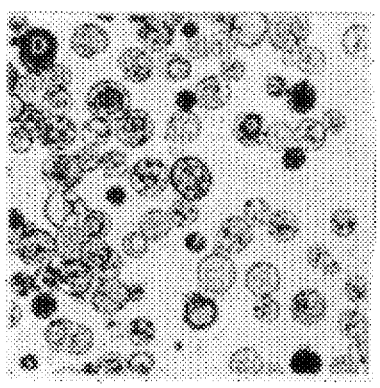
Figure 1E:
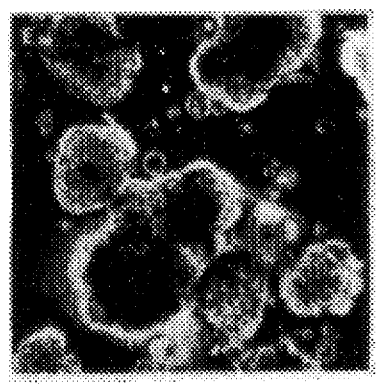
Figure 1F:
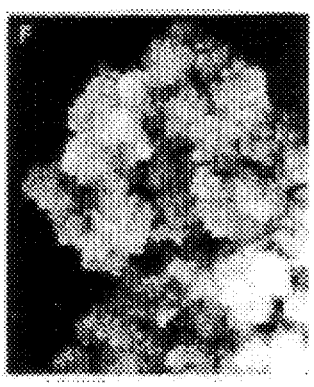
Figure 1G:
Figure 1H:
Figure 1I:
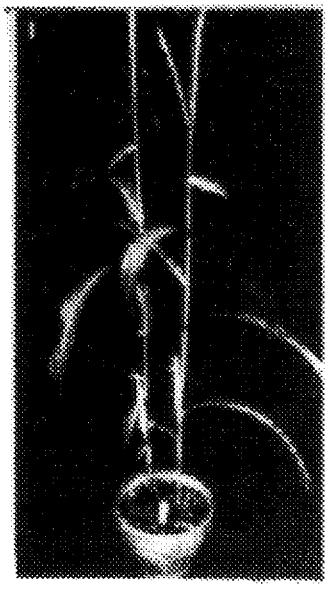
Figure 1K:

FIGS. 1 A–K: shows the various cell types and developmental stages involved in culturing DSM 6009, the DSM 6009 embryogenic maize culture and the regeneration of normal plants from it via the protoplast culture process, as follows:

FIG. 1A: established early embryogenic culture;

FIG. 1B: semi-fine suspension culture ready for protoplast isolation;

FIG. 1C: protoplasts 6 hours after isolation;

FIG. 1D: the first divisions 32 hours after isolation;

FIG. 1E: colonies 8 days after isolation;

FIGS. 1F and 1G: early and late embryogenic cultures from protoplasts after 2 months, respectively;

FIGS. 1H and 1I: regenerated plants from protoplasts before (FIG. 1H) and after (FIG. 1I) transplantation into soil;

FIG. 1J: mature protoplast-derived plants with seed, 3½ months after transfer into soil.

Further Definitions for Examples 5–12
Protoplast isolation medium (100 ml)

| | |
|---|---|
| Cellulase Onozuka R (Meiji Seika, Japan) | 800 mg |
| Pectolyase Y3 | 40 mg |
| $KNO_3$ | 200 mg |
| $KH_2PO_4$ | 136 mg |
| $K_2HPO_4$ | 47 mg |
| $CaCl_2.2H_2O$ | 147 mg |
| $MgSO_4.7H_2O$ | 250 mg |
| Bovine serum albumin (BSA) | 20 mg |
| Glucose | 4000 mg |
| Fructose | 4000 mg |
| Sucrose | 1000 mg |
| pH | 5.8 |
| Osmolarity | 660 mOsm. |

Protoplast wash solution 1: as above but without cellulase, pectolyase and BSA.

| Transformation buffer | |
|---|---|
| a) Glucose | 0.5 M |
| MES | 0.1% |
| $MgCl_2.6H_2O$ | 25 mM |
| pH | 5.8 |
| adjust to 600 mOsm. | |
| b) PEG 6000 solution | |
| Glucose | 0.5 M |
| $MgCl_2.6H_2O$ | 100 mM |
| Hepes | 20 mM |
| pH | 6.5 |

PEG 6000 is added to the above buffer under b), shortly before the solution is used (40% by weight of PEG). The PEG solution is filtered through a 0.45 μm sterile filter.

W5 Solution

| | |
|---|---|
| $CaCl_2$ | 125 mN |
| NaCl | 150 mN |
| HCl | 5 mN |
| Glucose | 50 mM |

Protoplast culture medium (amounts in mg/l)

| | |
|---|---|
| $KN_3$ | 3000 |
| $(NH_4)_2.7H_2O$ | 500 |
| $MgSO_4.7H_2O$ | 350 |
| $KH_2PO_4$ | 400 |
| $CaCl_2.2H_2O$ | 300 |

Fe EDTA and trace elements as in the Murashige-Skoog medium (Physiol. Plant, 15, 473 (1962); incorporated herein by reference)

| | |
|---|---|
| m-Inositol | 100 |
| Thiamine HCl | 1.0 |
| Nicotinamide | 0.5 |
| Pyridoxine HCl | 0.5 |
| Glycine | 2.0 |
| Glucuronic acid | 750 |
| Galacturonic acid | 750 |

-continued

| | |
|---|---|
| Galactose | 500 |
| Maltose | 500 |
| Glucose | 36,000 |
| Fructose | 36,000 |
| Sucrose | 30,000 |
| Asparagine | 500 |
| Glutamine | 100 |
| Proline | 300 |
| Casein hydrolyzate | 500 |
| 2,4-Dichlorophenoxyacetic acid (2,4-D) | 0.5 |
| pH | 5.8 |
| Osmolarity | 600 mOsm |

Example 5

Production of Protoplasts of Cell Line DSM 6009

Protoplast Isolation

About 2–4 days, preferably 3 days, after the last medium change of the suspension culture, the liquid medium was aspirated off, and the cells which remain were rinsed with 50 ml of protoplast wash solution 1 and again sucked dry. Ten ml of protoplast isolation medium were added per 2 g of the harvested biomass. The resuspended cells and cell aggregates were incubated for 4 to 6 hours at 27°±2° C. in the dark, with gentle shaking (30 to 40 rpm).

Protoplast Purification

As soon as at least 1 million protoplasts/ml emerged (observation under the microscope), the suspension was passed through a stainless-steel and nylon screen of 200 and 45 μm mesh size, respectively. The combination of one 100 μm screen and one 60 μm screen allowed the cell aggregates to be separated equally well. The protoplast containing filtrate was assessed under the microscope.

The filtrate generally contained 98–99% protoplast. The remaining 1–2% was undigested single cells. Protoplast preparations with this degree of purity were used for transformation experiments without additional gradient centrifugation. The protoplasts were sedimented by centrifugation, 1000 rpm in a swing-out rotor (100×g, 3 min). The supernatant was discarded and the protoplasts were resuspended in wash solution 1. The centrifugation step was repeated and the protoplasts were then resuspended in the transformation buffer.

Example 6

Cloning of the Phosphinothricin Acetyltransferase Gene

For the transformation step, the synthetic phosphinothricin acetyltransferase gene (SEQ ID NO:1/SEQ ID NO:2) shown in FIG. 3 was used under the control of the promoter from the 35S transcript of the cauliflower mosaic virus shown in FIG. 4 (the phosphinothricin acetyltransferase structural gene (SEQ ID NO:3/SEQ ID NO:4/SEQ ID NO:5)) was cloned into the SalI cleavage site of pDH51 mentioned), or the synthetic gene from European Patent Application EP 0 275 957, incorporated herein by reference, was used. The chimeric gene comprising 35S promoter structural gene and 35S terminator was integrated into the EcoRI site of the pUC18 polylinker. (See, Franck et al., Cell 21, 285 (1980), Wohlleben et al., Gene 80, 25 (1988), and Pietrzak et al., Nucleic Acids Res. 14, 5857 (1986); each incorporated herein by reference).

In most of the experiments, uncut pUC18-35S-acetyltransferase plasmid was used. In some individual experiments, the plasmid was cleaved with EcoRI, and the mixture of linearized pUC18 plasmid and the 1.3 kb, 35S-acetyl-transferase insert was used for transformation.

Example 7

Protoplast Transformation

Ten ml portions of the protoplasts which were resuspended in transformation buffer were introduced into 50 ml polyallomer tubes at a titer of $0.5–1.0 \times 10^6$ protoplasts/ml. The DNA which was used for transformation was dissolved in tris-EDTA (TE) buffer. Twenty μg of plasmid DNA were added per ml of protoplast suspension. After the DNA has been added, the protoplast suspension was shaken carefully to distribute the DNA homogeneously in the solution. Immediately afterwards, five ml of PEG solution were added dropwise.

The PEG solution was distributed homogeneously by carefully tilting the tubes. After this, another 5 ml of PEG solution were added, and the homogeneous mixing was repeated. The protoplasts remain in the PEG solution for 20 minutes at 25°±2° C. The protoplasts were then sedimented by centrifugation for 3 minutes (100 g=1000 rpm). The supernatant was discarded. The protoplasts were washed in 20 ml of W5 in solution by careful shaking and then recentrifuged. After this, they were resuspended in 20 ml of protoplast culture medium, recentrifuged and again resuspended in culture medium. The titer was adjusted to 6–8× $10^5$ protoplasts/ml, and the protoplasts were cultured in Petri dishes (diameter 60 mm, height 15 mm) in 3 ml portions. The Petri dishes were sealed with Parafilm were placed in the dark at 25°±2° C.

Example 8

Protoplast Culture

During the first 2–3 weeks after protoplast isolation and protoplast transformation, the protoplasts were cultured without the addition of fresh medium. As soon as the cells which have regenerated from the protoplasts have developed into cell aggregates with more than 20–50 cells, 1 ml of fresh protoplast culture medium containing sucrose (90 g/l) as osmotic agent was added.

Example 9

Selection of Transformed Maize Cells and Plant Regeneration

About 3–10 days after fresh medium was added, the protoplast-derived cell aggregates were plated onto agar media containing 100 mg/l L-phosphinothricin. Media which were suitable were N6 medium with the vitamins of the protoplast culture medium, 90 g/l sucrose and 1.0 mg/l 2,4-D, or an analogous medium, for example containing the macro- and micro-nutrient salts of the MS medium (Murashige+Skoog 1962; incorporated herein by reference).

The calli which originated from stably transformed protoplasts can continue their growth unhindered on the selective medium. After 3–5 weeks, preferably 4 weeks, the transgenic calli can be transferred to fresh selection medium, which also contains 100 mg/l L-phosphinothricin, but which no longer contains auxin. In the course of 3–5 weeks, approximately 50% of transgenic maize call which have integrated the L-phosphinothricin acetyltransferase gene into their genome differentiate first plants on this medium in the presence of L-phosphinothricin.

Example 10

Raising Transgenic Regenerated Plants

The embryogenic transformed maize tissue was cultured on hormone-free N6 medium (Chu C. C. et al., Sci. Sin. 16, 659, (1975); incorporated herein by reference) in the presence of $5 \times 10^{-4}$M L-phosphinothricin. On this medium, maize embryos which express the phosphinothricin acetyltransferase gene (PAT gene) at a sufficient level develop into plants. Untransformed embryos, or embryos whose PAT activity was only very weak, died. As soon as the leaves of the in vitro plants had a length of 4–6 mm, they were transferred into soil. Remains of agar on the roots were washed off, and the plants were then planted into a mixture of loam, sand, vermiculite and standard soil in the ratio 3:1:1:1 and adapted to soil culture after transplanting at 90–100% relative atmospheric humidity for the first 3 days. The plants were raised in a controlled-environment cabinet with a 14 h light period, approximately 25,000 lux at plant level, at a daytime/nighttime temperature of $23°/17° \pm 1°$ C. The adapted plants were cultured at an atmospheric humidity of $65 \pm 5\%$.

Example 11

Demonstration of the Expression of the Transferred Phosphinothricin Acetyltransferase Gene About 3–4 weeks after transfer into soil, transgenic regenerated plants, and, as controls, regenerated plants from calli which had not been treated with DNA, were sprayed with phosphinothricin in the commercially available formulations (Basta®). An amount of phosphinothricin was used which corresponds to the treatment with 2.0 kg of active ingredient/ ha. The herbicide was applied in an amount of water of 50 ml/m² (=500 l/ha). The damage by this amount of phosphinothricin of plants without PAT activity in the course of 7–10 days was either nonexistent, depending on the degree to which the gene was expressed, or, in the case of low PAT activity, local leaf spots appear which, however, did not affect the growth of the treated plants to a measurable extent.

Batches of 100 mg samples of maize calli and leaf tissue were frozen in 1.5 ml reaction vessels in liquid nitrogen and homogenized using a stainless steel micropestle which was adapted to suit the shape of the vessel. One hundred µl of tris-EDTA buffer (50 mM of tris/2 mM of EDTA, pH 7.5) were added. The homogenate was centrifuged for one minute in an Eppendorf centrifuge at 12,000 rpm. The clear supernatant was pipetted off, and the pellet was discarded. The protein content of the crude extract was determined by means of the Bio-Rad protein assay. For the PAT assay, aliquots of crude extracts were withdrawn, each of which contain 20 µg of protein. Acetyl-CoA and 14C L-phosphinothricin were added to the extracts. The final concentration in the incubation mixture was 1 mM in the case of acetyl-CoA and 0.1 mM in the case of 14C L-phosphinothricin. The samples were mixed briefly and incubated for 1 hour at 37° C. After this, the enzyme reaction was stopped by adding ½ volume of 12% trichloroacetic acid, and the samples were mixed thoroughly and placed on ice for 10 minutes. After this, they were centrifuged for 10 minutes at 12,000 rpm, and the supernatant was used for thin-layer chromatography. On a thin-layer plate (Cellulose F254, manufactured by Merck®), portions of 6 µl of the incubation mixtures were applied, and also the reference substances 14C phosphinothricin and 14C acetylphosphinothricin. The mobile phase used for the thin-layer chromatography was either n-propanol: 25% $NH_3$ (3:2) or pyridine:n-butanol:glacial acetic acid:water (3:5:1:4).

The dried thin-layer plate was wrapped in plastic film and exposed in an Bray film cassette. On the developed X-ray film, the PAT activity can be recognized by the acetylphosphinothricin band (which only occur in transgenic tissue). In the abovementioned mobile phases, phosphinothricin and acetylphosphinothricin can be separated successfully by means of thin-layer chromatography.

Example 12

Transmission of the Transferred Gene to the Progeny of the Regenerated Plants Pollen of transformants which tolerate application of a glufosinate dosage rate of 2 kg a.i./ha without damage and which unambiguously show PAT activity in the PAT enzyme assay, was used for pollinating stigmata of various inbred lines, inter alia B73, LH19, LH82, LH51 or Mo17. Since only nucleus-encoded genes can be transmitted via the pollen, it was thereby possible to check whether the transferred gene had been integrated in the nuclear genome. Only in this case can expression of the gene in the progeny and mendelian inheritance be expected.

a) Test on Immature Embryos

About 12–16 days after pollination, immature embryos were excised from the caryopses under sterile conditions. The isolated embryos were cultured on hormone-free MS or $N_6$ agar medium which contained 9% of sucrose and 100 mg/l ammonium salt of L-phosphinothricin (glufosinate ammonium). The embryos were cultured on the medium in such a way that the scutellum was in contact with the agar. They were subsequently cultured at 2000–5000 lux (12 h/day) at $75° \pm 2°$ C. On this medium, embryos without PAT gene capable of expression died off within 14 days without previously having started to germinate. Table 1 shows the behavior of the first hybrid filial generation ($t_1$ hybrids) of three different transformants.

TABLE 1

| Behavior of immature embryos from crosses of transgenic father plants with non-transgenic inbred lines | | | |
|---|---|---|---|
| Pollen donor | Isolated embryos | Dying embryos | Developing embryos |
| Transformant 2 | 20 | 9 | 11 |
| Transformant 5 | 20 | 12 | 8 |
| Transformant 9 | 100 | 47 | 53 |

The embryos which developed and which germinated in the presence of $5 \cdot 10^{-4}$M L-phosphinothricin developed normal roots as well as green leaves on this medium. The plants can be transferred into soil analogously to the in vitro plants developed from somatic embryos. These plants transmitted the PAT gene to the $t_2$ generation when pollen of the $t_1$ plants was placed on stigmata of non-transgenic mother plants.

b) Seedling Test

Mature seeds from the above-described crosses were dried (>15% water content) and sown (20,000 lux for 12 h, 22° C. daytime/16° C. nighttime temperature). As soon as the seedlings have reached the 2–3 leaf stage, they were sprayed with a 1% solution of the commercially available product Basta® analogously to the regenerated plants (cf. Example 10).

The result can be seen from Table 2.

TABLE 2

| Pollen donor | Seedlings tested | Seedlings after application of 2 kg of glufosinate/ha | |
|---|---|---|---|
| | | Undamaged | Dead |
| Transformant 9 | 29 | 15 | 14 |
| Transformant 13 | 20 | 11 | 9 |
| Transformant 14 | 39 | 17 | 22 |

The segregation ratios were consistent with the assumption that some transformants only possess one functional PAT gene in their genome.

On Jun. 12, 1990, seeds of Transformant No. 14 were deposited at the National Collections of Industrial and Marine Bacteria Ltd. (NCIMB), Aberdeen, GB, under the conditions of the Budapest Treaty, with the registration number NCIMB 40291.

Having thus described in detail preferred embodiments of the present invention, it is to be understood that the invention defined by the appended claims is not to be limited by particular details set forth in the above description as many apparent variations thereof are possible without departing from the spirit or scope thereof.

---

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 793 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

```
GAATTCCCAT GGAGTCAAAG ATTCAAATAG AGGACCTAAC AGAACTCGCC GTAAAGACTG      60
GCGAACAGTT CATACAGAGT CTCTTACGAC TCAATGACAA GAAGAAAATC TTCGTCAACA     120
TGGTGGAGCA CGACACGCTT GTCTACTCCA AAAATATCAA AGATACAGTC TCAGAAGACC     180
AAAGGGCAAT TGAGACTTTT CAACAAAGGG TAATATCCGG AAACCTCCTC GGATTCCATT     240
GCCCAGCTAT CTGTCACTTT ATTGTGAAGA TAGTGGAAAA GGAAGGTGGC TCCTACAAAT     300
GCCATCATTG CGATAAAGGA AAGGCCATCG TTGAAGATGC CTCTGCCGAC AGTGGTCCCA     360
AAGATGGACC CCCACCCACG AGGAGCATCG TGGAAAAAGA AGACGTTCCA ACCACGTCTT     420
CAAAGCAAGT GGATTGATGT GATATCTCCA CTGACGTAAG GGATGACGCA CAATCCCACT     480
ATCCTTCGCA AGACCCTTCC TCTATATAAG GAAGTTCATT TCATTTGGAG AGGACAGGGT     540
ACCCGGGGAT CCTCTAGAGT CGACCTGCAG GCATGCCGCT GAAATCACCA GTCTCTCTCT     600
ACAAATCTAT CTCTCTCTAT AATAATGTGT GAGTAGTTCC CAGATAAGGG AATTAGGGTT     660
CTTATAGGGT TTCGCTCATG TGTTGAGCAT ATAAGAAACC CTTAGTATGT ATTTGTATTT     720
GTAAAATACT TCTATCAATA AAATTTCTAA TTCCTAAAAC CAAAATCCAG TGGGTACCGA     780
GCTCGAATTC AAG                                                        793
```

( 2 ) INFORMATION FOR SEQ ID NO:2:

( i ) SEQUENCE CHARACTERISTICS:
        ( A ) LENGTH: 793 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
CTTAAGGGTA CCTCAGTTTC TAAGTTTATC TCCTGGATTG TCTTGAGCGG CATTTCTGAC       60
```

| | | | |
|---|---|---|---|
| CGCTTGTCAA GTATGTCTCA GAGAATGCTG AGTTACTGTT CTTCTTTTAG AAGCAGTTGT | 120 |
| ACCACCTCGT GCTGTGCGAA CAGATGAGGT TTTTATAGTT TCTATGTCAG AGTCTTCTGG | 180 |
| TTTCCCGTTA ACTCTGAAAA GTTGTTTCCC ATTATAGGCC TTTGGAGGAG CCTAAGGTAA | 240 |
| CGGGTCGATA GACAGTGAAA TAACACTTCT ATCACCTTTT CCTTCCACCG AGGATGTTTA | 300 |
| CGGTAGTAAC GCTATTTCCT TTCCGGTAGC AACTTCTACG GAGACGGCTG TCACCAGGGT | 360 |
| TTCTACCTGG GGGTGGGTGC TCCTCGTAGC ACCTTTTCT TCTGCAAGGT TGGTGCAGAA | 420 |
| GTTTCGTTCA CCTAACTACA CTATAGAGGT GACTGCATTC CCTACTGCGT GTTAGGGTGA | 480 |
| TAGGAAGCGT TCTGGGAAGG AGATATATTC CTTCAAGTAA AGTAAACCTC TCCTGTCCCA | 540 |
| TGGGCCCCTA GGAGATCTCA GCTGGACGTC CGTACGGCGA CTTTAGTGGT CAGAGACAGA | 600 |
| TGTTTAGATA GAGAGAGATA TTATTACACA CTCATCAAGG GTCTATTCCC TTAATCCCAA | 660 |
| GAATATCCCA AAGCGAGTAC ACAACTCGTA TATTCTTTGG GAATCATACA TAAACATAAA | 720 |
| CATTTTATGA AGATAGTTAT TTTAAAGATT AAGGATTTTG GTTTAGGTC ACCCATGGCT | 780 |
| CGAGCTTAAG TTC | 793 |

( 2 ) INFORMATION FOR SEQ ID NO:3:

( i ) SEQUENCE CHARACTERISTICS:
( A ) LENGTH: 564 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 7..555

( x i ) SEQUENCE DESCRIPTION: SEQ ID NO:3:

```
GTCGAC ATG TCT CCG GAG AGG AGA CCA GTT GAG ATT AGG CCA GCT ACA        48
       Met Ser Pro Glu Arg Arg Pro Val Glu Ile Arg Pro Ala Thr
       1               5                   10

GCA GCT GAT ATG GCC GCG GTT TGT GAT ATC GTT AAC CAT TAC ATT GAG       96
Ala Ala Asp Met Ala Ala Val Cys Asp Ile Val Asn His Tyr Ile Glu
15              20                  25                  30

ACG TCT ACA GTG AAC TTT AGG ACA GAG CCA CAA ACA CCA CAA GAG TGG     144
Thr Ser Thr Val Asn Phe Arg Thr Glu Pro Gln Thr Pro Gln Glu Trp
            35                  40                  45

ATT GAT GAT CTA GAG AGG TTG CAA GAT AGA TAC CCT TGG TTG GTT GCT     192
Ile Asp Asp Leu Glu Arg Leu Gln Asp Arg Tyr Pro Trp Leu Val Ala
                50                  55                  60

GAG GTT GAG GGT GTT GTG GCT GGT ATT GCT TAC GCT GGG CCC TGG AAG     240
Glu Val Glu Gly Val Val Ala Gly Ile Ala Tyr Ala Gly Pro Trp Lys
                65                  70                  75

GCT AGG AAC GCT TAC GAT TGG ACA GTT GAG AGT ACT GTT TAC GTG TCA     288
Ala Arg Asn Ala Tyr Asp Trp Thr Val Glu Ser Thr Val Tyr Val Ser
        80                  85                  90

CAT AGG CAT CAA AGG TTG GGC CTA GGA TCC ACA TTG TAC ACA CAT TTG     336
His Arg His Gln Arg Leu Gly Leu Gly Ser Thr Leu Tyr Thr His Leu
95                  100                 105                 110

CTT AAG TCT ATG GAG GCG CAA GGT TTT AAG TCT GTG GTT GCT GTT ATA     384
Leu Lys Ser Met Glu Ala Gln Gly Phe Lys Ser Val Val Ala Val Ile
                115                 120                 125

GGC CTT CCA AAC GAT CCA TCT GTT AGG TTG CAT GAG GCT TTG GGA TAC     432
Gly Leu Pro Asn Asp Pro Ser Val Arg Leu His Glu Ala Leu Gly Tyr
            130                 135                 140

ACA GCC CGG GGT ACA TTG CGC GCA GCT GGA TAC AAG CAT GGT GGA TGG     480
Thr Ala Arg Gly Thr Leu Arg Ala Ala Gly Tyr Lys His Gly Gly Trp
                145                 150                 155
```

```
CAT GAT GTT GGT TTT TGG CAA AGG GAT TTT GAG TTG CCA GCT CCT CCA      528
His Asp Val Gly Phe Trp Gln Arg Asp Phe Glu Leu Pro Ala Pro Pro
    160                 165                 170

AGG CCA GTT AGG CCA GTT ACC CAG ATC TGAGTCGAC                        564
Arg Pro Val Arg Pro Val Thr Gln Ile
175             180
```

( 2 ) INFORMATION FOR SEQ ID NO:4:

( i ) SEQUENCE CHARACTERISTICS:
        ( A ) LENGTH: 183 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ser Pro Glu Arg Arg Pro Val Glu Ile Arg Pro Ala Thr Ala Ala
1               5                   10                  15

Asp Met Ala Ala Val Cys Asp Ile Val Asn His Tyr Ile Glu Thr Ser
            20                  25                  30

Thr Val Asn Phe Arg Thr Glu Pro Gln Thr Pro Gln Glu Trp Ile Asp
        35                  40                  45

Asp Leu Glu Arg Leu Gln Asp Arg Tyr Pro Trp Leu Val Ala Glu Val
    50                  55                  60

Glu Gly Val Val Ala Gly Ile Ala Tyr Ala Gly Pro Trp Lys Ala Arg
65                  70                  75                  80

Asn Ala Tyr Asp Trp Thr Val Glu Ser Thr Val Tyr Val Ser His Arg
                85                  90                  95

His Gln Arg Leu Gly Leu Gly Ser Thr Leu Tyr Thr His Leu Leu Lys
                100                 105                 110

Ser Met Glu Ala Gln Gly Phe Lys Ser Val Val Ala Val Ile Gly Leu
            115                 120                 125

Pro Asn Asp Pro Ser Val Arg Leu His Glu Ala Leu Gly Tyr Thr Ala
        130                 135                 140

Arg Gly Thr Leu Arg Ala Ala Gly Tyr Lys His Gly Gly Trp His Asp
145                 150                 155                 160

Val Gly Phe Trp Gln Arg Asp Phe Glu Leu Pro Ala Pro Pro Arg Pro
                165                 170                 175

Val Arg Pro Val Thr Gln Ile
                180
```

( 2 ) INFORMATION FOR SEQ ID NO:5:

( i ) SEQUENCE CHARACTERISTICS:
        ( A ) LENGTH: 564 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:5:

```
GTCGACTCAG ATCTGGGTAA CTGGCCTAAC TGGCCTTGGA GGAGCTGGCA ACTCAAAATC      60

CCTTTGCCAA AAACCAACAT CATGCCATCC ACCATGCTTG TATCCAGCTG CGCGCAATGT     120

ACCCCGGGCT GTGTATCCCA AAGCCTCATG CAACCTAACA GATGGATCGT TTGGAAGGCC     180

TATAACAGCA ACCACAGACT TAAAACCTTG CGCCTCCATA GACTTAAGCA AATGTGTGTA     240

CAATGTGGAT CCTAGGCCCA ACCTTTGATG CCTATGTGAC ACGTAAACAG TACTCTCAAC     300

TGTCCAATCG TAAGCGTTCC TAGCCTTCCA GGGCCCAGCG TAAGCAATAC CAGCCACAAC     360
```

| | | | | | | |
|---|---|---|---|---|---|---|
| ACCCTCAACC | TCAGCAACCA | ACCAAGGGTA | TCTATCTTGC | AACCTCTCTA | GATCATCAAT | 420 |
| CCACTCTTGT | GGTGTTTGTG | GCTCTGTCCT | AAAGTTCACT | GTAGACGTCT | CAATGTAATG | 480 |
| GTTAACGATA | TCACAAACCG | CGGCCATATC | AGCTGCTGTA | GCTGGCCTAA | TCTCAACTGG | 540 |
| TCTCCTCTCC | GGAGACATGT | CGAC | | | | 564 |

What is claimed is:

1. A *Zea mays* (L.) cell line which is auxin-autotrophic and from which protoplasts, which can reproducibly and stably regenerate into fertile plants, can be produced.

2. The cell line having the name and accession number DSM 6009.

3. An auxin-autotropic embryonic cell culture produced from the *Zea mays* cell line as claimed in claim 1.

4. Auxin-autotrophic protoplast produced from the *Zea mays* cell line as claimed in claim 1.

5. A method for producing a callus culture of *Zea mays* (l.) from which protoplasts can be isolated, which protoplasts are capable of being regenerated into fertile plants, which method comprises the steps of:
   a) obtaining callus which is auxin-autotrophic, relatively non-mucilaginous, granular and friable on a callus maintenance medium; and
   b) growing the callus of step a) on a callus maintenance medium.

6. A fertile *Zea mays* (L.) plant having cells which can be cultured and maintained on auxin-free media.

7. A fertile *Zea mays* (L.) plant of claim 6, derived from a cell line named and having accession number DSM 6009, and having cells which can be cultured and maintained on auxin-free media.

8. An auxin-autotrophic *Zea mays* (L.) cell line from which fertile *Zea mays* (L.) plants can be obtained.

9. An auxin-autotrophic protoplast from the cell line of claim 8.

10. A *Zea mays* (L.) plant from the cell line of claim 1 having cells which can be cultured and maintained on auxin-free media.

11. Progeny from the plant of claim 6 which have cells which can be cultured and maintained on auxin-free media.

12. Progeny from the plant of claim 10 which have cells which can be cultured and maintained on auxin-free media.

13. Auxin-autotrophic callus from the cell line of claim 1.

14. Auxin-autotrophic callus from the cell line of claim 8.

* * * * *

UNITED STATES PATENT AND TRADEMARK OFFICE
CERTIFICATE OF CORRECTION

PATENT NO. : 5,792,936
DATED : August 11,1998
INVENTOR(S) : Budits et al.

It is certified that error appears in the above-identified patent and that said Letters Patent is hereby corrected as shown below:

On the title page, item [56] add the following:

--5,550,381, Adams et al.-- and --5,489,520, Adams et al.--

Signed and Sealed this

Twenty-seventh Day of July, 1999

Attest:

Q. TODD DICKINSON

*Attesting Officer*  *Acting Commissioner of Patents and Trademarks*